US009968718B2

(12) United States Patent
Yoshida et al.

(10) Patent No.: US 9,968,718 B2
(45) Date of Patent: *May 15, 2018

(54) METHOD AND SYSTEM FOR REMOVING OXYGEN AND CARBON DIOXIDE DURING RED CELL BLOOD PROCESSING USING AN INERT CARRIER GAS AND MANIFOLD ASSEMBLY

(71) Applicant: New Health Sciences, Inc., Bethesda, MD (US)

(72) Inventors: Tatsuro Yoshida, West Newton, MA (US); Paul Vernucci, Billerica, MA (US)

(73) Assignee: New Health Sciences, Inc., Bethesda, MD (US)

( * ) Notice: Subject to any disclaimer, the term of this patent is extended or adjusted under 35 U.S.C. 154(b) by 538 days.

This patent is subject to a terminal disclaimer.

(21) Appl. No.: 14/614,045

(22) Filed: Feb. 4, 2015

(65) Prior Publication Data

US 2015/0147744 A1     May 28, 2015

Related U.S. Application Data

(63) Continuation of application No. 13/432,810, filed on Mar. 28, 2012, now Pat. No. 9,067,004.

(Continued)

(51) Int. Cl.
*A61M 1/00* (2006.01)
*A61M 1/02* (2006.01)
*A61M 1/38* (2006.01)

(52) U.S. Cl.
CPC ........ *A61M 1/0272* (2013.01); *A61M 1/0281* (2013.01); *A61M 1/38* (2013.01);
(Continued)

(58) Field of Classification Search
CPC .... A61M 1/0272; A61M 1/0281; A61M 1/38; A61M 2202/0208; A61M 2202/0225; A61M 2202/0439
See application file for complete search history.

(56) References Cited

U.S. PATENT DOCUMENTS 3,064,647 A   11/1962  Earl
3,361,041 A    1/1968  Grob
(Continued)

FOREIGN PATENT DOCUMENTS

CA    2477946        9/2003
CN    1195965 A     10/1998
(Continued)

OTHER PUBLICATIONS

Dumont et al., "CO2-dependent metabolic modulation in red blood cells stored under anaerobic conditions," *Transfusion*, 56(2):392-403 (2016).

(Continued)

*Primary Examiner* — Benjamin Klein
(74) *Attorney, Agent, or Firm* — Arnold & Porter Kaye Scholer LLP

(57) ABSTRACT

A portable assembly for processing red blood cells RBCs including a disposable blood collection set including a blood bag, an anaerobic storage bag and an oxygen and/or oxygen and carbon dioxide depletion device disposed between the blood collection bag and anaerobic storage bag. The portable assembly further provides for a gas circulation device in fluid communication with the oxygen or oxygen and carbon dioxide depletion device, The gas circulation device includes a pressure source that is able circulate flushing gas through the depletion device as RBCs pass from the blood collection bag, through the depletion device and into the anaerobic storage bag.

20 Claims, 8 Drawing Sheets

Related U.S. Application Data

(60) Provisional application No. 61/468,377, filed on Mar. 28, 2011.

(52) U.S. Cl.
CPC ............. *A61M 2202/0208* (2013.01); *A61M 2202/0225* (2013.01); *A61M 2202/0439* (2013.01)

(56) References Cited

U.S. PATENT DOCUMENTS

| | | |
|---|---|---|
| 3,668,837 A | 6/1972 | Gross |
| 3,668,838 A | 6/1972 | McNeil et al. |
| 3,803,810 A | 4/1974 | Rosenberg |
| 3,910,841 A | 10/1975 | Esmond |
| 3,942,529 A | 3/1976 | Waage |
| 4,086,924 A | 5/1978 | Latham, Jr. |
| 4,131,200 A | 12/1978 | Rinfret |
| 4,222,379 A | 9/1980 | Smith |
| 4,225,439 A | 9/1980 | Spranger |
| 4,228,032 A | 10/1980 | Talcott |
| 4,253,458 A | 3/1981 | Bacehowski et al. |
| 4,256,692 A | 3/1981 | Cover |
| 4,262,581 A | 4/1981 | Ferrell |
| 4,300,559 A | 11/1981 | Gajewski et al. |
| 4,342,723 A | 8/1982 | Sado et al. |
| 4,366,179 A | 12/1982 | Nawata et al. |
| 4,370,160 A | 1/1983 | Ziemelis |
| 4,381,775 A | 5/1983 | Nose et al. |
| 4,386,069 A | 5/1983 | Estep |
| 4,398,642 A | 8/1983 | Okudaira et al. |
| 4,440,815 A | 4/1984 | Zomorodi et al. |
| 4,455,299 A | 6/1984 | Grode |
| 4,540,416 A | 9/1985 | Hattori et al. |
| 4,568,328 A | 2/1986 | King et al. |
| 4,572,899 A | 2/1986 | Walker et al. |
| 4,585,735 A | 4/1986 | Meryman et al. |
| 4,629,544 A | 12/1986 | Bonaventura et al. |
| 4,654,053 A | 3/1987 | Sievers et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,731,978 A | 5/1988 | Martensson |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,798,728 A | 1/1989 | Sugisawa |
| 4,837,047 A | 6/1989 | Sato et al. |
| 4,859,360 A | 8/1989 | Suzuki et al. |
| 4,861,867 A | 8/1989 | Estep |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 4,986,837 A | 1/1991 | Shibata |
| 4,998,990 A | 3/1991 | Richter et al. |
| 5,000,848 A | 3/1991 | Hodgins et al. |
| 5,023,054 A | 6/1991 | Sato et al. |
| 5,037,419 A | 8/1991 | Valentine et al. |
| 5,120,659 A | 6/1992 | King et al. |
| 5,139,668 A | 8/1992 | Pan et al. |
| 5,143,763 A | 9/1992 | Yamada et al. |
| 5,152,905 A | 10/1992 | Pall et al. |
| 5,192,320 A | 3/1993 | Anazawa et al. |
| 5,194,158 A | 3/1993 | Matson |
| 5,208,335 A | 5/1993 | Ramprasad et al. |
| 5,229,012 A | 7/1993 | Pall et al. |
| 5,254,248 A | 10/1993 | Nakamura et al. |
| 5,328,268 A | 7/1994 | LaFleur |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,368,808 A | 11/1994 | Koike et al. |
| 5,382,526 A | 1/1995 | Gajewski et al. |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,686,304 A | 11/1997 | Codner |
| 5,691,452 A | 11/1997 | Gawryl et al. |
| 5,693,122 A | 12/1997 | Berndt |
| 5,693,230 A | 12/1997 | Asher |
| 5,698,250 A | 12/1997 | DelDuca et al. |
| 5,709,472 A | 1/1998 | Prusik et al. |
| 5,744,056 A | 4/1998 | Venkateshwaran et al. |
| 5,730,989 A | 5/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,076,664 A | 6/2000 | Yeager |
| 6,080,322 A | 6/2000 | Deniega et al. |
| 6,090,062 A | 7/2000 | Sood et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,482,585 B2 | 11/2002 | Dottori |
| 6,527,957 B1 | 3/2003 | Deniega et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |

(56) References Cited

U.S. PATENT DOCUMENTS

| | | |
|---|---|---|
| 6,703,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 9,005,343 B2 | 4/2015 | Yoshida et al. |
| 9,067,004 B2 * | 6/2015 | Yoshida ............... A61M 1/0272 |
| 9,199,016 B2 | 12/2015 | Yoshida et al. |
| 9,296,990 B2 | 3/2016 | Federspiel et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 * | 8/2003 | Bitensky ............... A01N 1/0226 435/374 |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 * | 10/2006 | Robinson ............... A61M 1/30 210/787 |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0240569 A1 | 10/2007 | Ooya |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0243045 A1 | 10/2008 | Pasqualini |
| 2008/0276803 A1 | 11/2008 | Molaison et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004937 A1 | 1/2013 | Yoshida et al. |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2016/0007588 A1 | 1/2016 | Levesque et al. |

FOREIGN PATENT DOCUMENTS

| | | |
|---|---|---|
| CN | 2502700 Y | 7/2002 |
| CN | 1642628 A | 7/2005 |
| CN | 2780207 Y | 5/2006 |
| CN | 2894710 Y | 5/2007 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 109 447 B1 | 10/2003 |
| EP | 1 891 999 A1 | 2/2008 |
| FR | 2 581 289 A1 | 11/1986 |
| GB | 1 044 649 A2 | 10/1966 |
| GB | 2283015 A1 | 4/1995 |
| JP | 58-194879 | 11/1983 |
| JP | 59-115349 | 7/1984 |
| JP | 61-109577 A | 5/1986 |
| JP | 63-63616 A | 3/1988 |
| JP | 01-104271 A | 4/1989 |
| JP | 5-503075 A | 5/1993 |
| JP | 5-503304 A | 6/1993 |
| JP | H05-148151 A | 6/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | 10/501443 A | 2/1998 |
| JP | 2000-516963 A | 12/2000 |
| JP | 2002-253936 A | 9/2002 |
| JP | 2004/089495 | 3/2004 |
| JP | 2005-535279 A | 11/2005 |
| JP | 2007-260393 A | 10/2007 |

(56) References Cited

FOREIGN PATENT DOCUMENTS

| | | |
|---|---|---|
| JP | 10/501443 | 2/2010 |
| JP | 2010-116626 | 5/2010 |
| JP | 2011-260393 A | 10/2011 |
| JP | 2013-500794 | 1/2013 |
| KR | 10-0721054 | 5/2006 |
| SU | 1718766 A1 | 1/1990 |
| WO | WO 81/02239 A1 | 8/1981 |
| WO | WO 86/00809 A1 | 2/1986 |
| WO | WO 89/02274 A1 | 3/1989 |
| WO | WO 91/04659 A1 | 4/1991 |
| WO | WO 92/08348 A1 | 5/1992 |
| WO | WO 95/29662 A2 | 11/1995 |
| WO | WO 96/29103 A1 | 9/1996 |
| WO | WO 96/29346 A1 | 9/1996 |
| WO | WO 96/29864 A1 | 10/1996 |
| WO | WO 96/39026 A1 | 12/1996 |
| WO | WO 1997/37628 A1 | 10/1997 |
| WO | WO 1998/046073 A1 | 10/1998 |
| WO | WO 98/51147 A1 | 11/1998 |
| WO | WO 1999/25726 A1 | 5/1999 |
| WO | WO 1999/29346 A1 | 6/1999 |
| WO | WO 99/48963 A2 | 9/1999 |
| WO | WO 2000/011946 A2 | 3/2000 |
| WO | WO 03/043419 A1 | 5/2003 |
| WO | WO 03/043571 A2 | 5/2003 |
| WO | WO 03/086577 A1 | 10/2003 |
| WO | WO 03/103390 A1 | 12/2003 |
| WO | WO 2004/043381 A2 | 5/2004 |
| WO | WO 2006/057473 A1 | 6/2006 |
| WO | WO 2006/088455 A1 | 8/2006 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/153441 A1 | 10/2013 |
| WO | WO 2013/177339 A1 | 11/2013 |
| WO | WO 2014/134503 A1 | 9/2014 |
| WO | WO 2016/145210 A1 | 9/2016 |
| WO | WO 2016/172645 A1 | 10/2016 |

OTHER PUBLICATIONS

Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).
Barbee et al., "The Fahraeus Effect," *Microvascular Research*, 3:6-16 (1971).
Barclay et al., "A Method for Detecting Chaos in Canine Myocardial Microcirculatory Red Cell Flux," *Microcirculation*, 7(5):335-346 (2000).
Bardy et al., "Technetium-99m Labeling by Means of Stannous Pyrophosphate: Application to Bleomycin and Red Blood Cells," *Journal of Nuclear Medicine*, 16(5):435-437 (1975).
Barras et al., "Einfluss der Rejuvenation auf die rheologischen Eigenschaften gelagerter Erythrozyten," *VASA*, 23(4):305-311 (1994).
Beutler et al., "Storage of red cell concentrates in CPD-A2 for 42 and 49 days," *The Journal of Laboratory and Clinical Medicine*, 102(1):53-62 (1983).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Burns et al., "Artificial microvascular network: a new tool for measuring rheologic properties of stored red blood cells," *Transfusion*, 52(5):1010-1023 (2012).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoScan (RheoScan-AnD300/RheoScan-D300), obtained on Dec. 11, 2012, from: http://www.rheoscan.com/products/products/products-01.html.
Chilton et al., "Privacy Protection of Health Information: Patient Rights and Pediatrician Responsibilities," *Pediatrics*, 104(4):973-977 (1999).
Cokelet et al., "Fabrication of in Vitro Microvascular Blood Flow Systems by Photolithography," *Microvascular Research*, 46:394-400 (1993).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
De Venuto et al., "Rejuvenation of Human Red Blood Cells During Liquid Storage," *Transfusion*, 14(4):338-344 (1974).
Deible et al., "Molecular barriers to biomaterial thrombosis by modification of surface proteins with polyethylene glycol," *Biomaterials*, 19:1885-1893 (1998).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumaswala et al., "Studies in Red Blood Cell Preservation: 9. The Role of Glutamine in Red Cell Preservation," *Vox Sang*, 67:255-259 (1994).
Dumont et al., "Anaerobic storage of red blood cells in a novel additive solution improves in vivo recovery," *Transfusion*, 49(3):458-464 (2009).
Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Extended European Search Report, dated Aug. 8, 2014 for European Patent Application No. 10823965.8.
Extended European Search Report, dated Oct. 23, 2014 for European Patent Application No. 11838889.1.
Extended European Search Report dated Nov. 4, 2014 in European Patent Application No. 12807324.4.
Extended European Search Report, dated Mar. 5, 2015 in European Patent Application No. 12821624.9.
Fahraeus et al., "The Viscosity of the Blood in Narrow Capillary Tubes," *Am. J. Physiol.*, 96(3):562-568 (1931).
Fang et al., Inhibition of Lipopolysaccharide-Associated Endotoxin Activities In Vitro and In Vivo by the Human Anti-Lipid A Monoclonal Antibody SdJ5-1.17.15, *Infection and Immunity*, 61(9):3873-3878 (1993).
Frame et al., "A System for Culture of Endothelial Cells in 20-50-μm Branching Tubes," *Microcirculation*, 2(4):377-385 (1995).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).

(56) References Cited

OTHER PUBLICATIONS

Gifford et al., "A detailed study of time-dependent changes in human red blood cells: from reticulocyte maturation to erythrocyte senescence," *British Journal of Haematology*, 135:395-404 (2006).

Gifford et al., "Parallel Microchannel-Based Measurements of Individual Erythrocyte Areas and Volumes," *Biophysical Journal*, 84:623-633 (2003).

Green et al., "10. Liposomal Vaccines," Immunobiology of Proteins and Peptides VII, Plenum Press, New York, pp. 83-92 (1995).

Greenwalt et al., "Studies in Red Blood Cell Preservation. 7. In vivo and in Vitro Studies with a Modified Phosphate-Ammonium Additive Solution," *Vox Sang*, 65:87-94 (1993).

Greenwalt et al., "Studies in Red Blood Cell Preservation. 8. Liquid Storage of Red Cells in Glycerol-Containing Additive Solution," *Vox. Sang*, 67:139-143 (1994).

Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).

Greenwalt et al., "The effect of hypotonicity, glutamine, and glycine on red cell preservation," *Transfusion*, 37:269-276 (1997).

Griffith, "Temporal chaos in the microcirculation," *Cardiovascular Research*, 31:342-358 (1996).

Hamasaki et al., "Acid-citrate-dextrose-phosphoenolpyruvate medium as a rejuvenant for blood storage," *Transfusion*, 23(1):1-7 (1983).

Hess et al., "Successful storage of RBCs for 9 weeks in a new additive solution," *Transfusion*, 40:1007-1011 (2000).

Hess, "Extended Liquid Storage of Red Blood Cells," Blood Donors and the Supply of Blood and Blood Products, National Academy Press, Washington, D.C., pp. 99-102 (1996).

Hess, "Storage of red blood cells under anaerobic conditions," *Vox Sanguinis*, 93:183 (2007).

Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).

Högman et al., "Effects of Oxygen on Red Cells during Liquid Storage at +4° C.," *Vox Sang.*, 51:27-34 (1986).

Högman et al., "Cell Shape and Total Adenylate Concentration as Important Factors for Posttransfusion Survival of Erythrocytes," *Biomed. Biochim. Acta*, 42:S327-S331 (1983).

Högman et al., "Effects of Oxygen and Mixing on red cells stored in plastic bags at +4° C.," *Biomed. Biochim. Acta.*, 46:S290-S294 (1987).

Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).

Holme et al., "Current Issues Related to the Quality of Stored RBC's," *Transfusion and Apheresis Science, Elsevier Science*, 33(1):55-61 (2005).

Huang et al., "Continuous Particle Separation Through Deterministic Lateral Displacement," *Science*, 304:987-990 (2004).

International Search Report completed on Apr. 26, 2011, in International Patent Application No. PCT/US2010/044045.

International Search Report completed on Feb. 12, 2012, in International Patent Application No. PCT/US11/59372.

International Search Report completed on Feb. 8, 2011, in International Patent Application No. PCT/US10/52084.

International Search Report completed on Jul. 10, 2014 in International Patent Application No. PCT/US2014/019537.

International Search Report completed on Jul. 8, 1996, in International Patent Application No. PCT/US96/09005.

International Search Report completed on Jun. 18, 2012, in International Patent Application No. PCT/US12/30930.

International Search Report completed on May 20, 2010, in International Patent Application No. PCT/US2010/31055.

International Search Report completed on Nov. 10, 2003, in International Patent Application No. PCT/US02/36735.

International Search Report completed on Nov. 22, 2010, in International Patent Application No. PCT/US2010/052376.

International Search Report completed on Nov. 9, 2012, in International Patent Application No. PCT/US12/45426.

International Search Report completed on Sep. 24, 2012, in International Patent Application No. PCT/US12/50380.

Jain, et al., "Determinants of Leukocyte Margination in Rectangular Microchannels," *PLoS One*, 4(9):1-8 (2009).

Jayasinghe et al., "Controlled deposition of nanoparticle clusters by electrohydrodynamic atomization," *Nanotechnology*, 15:1519-1523 (2004).

Jiang et al., "Microfluidic synthesis of monodisperse PDMS microbeads as discrete oxygen sensors," *Soft Matter*, 8:923-926 (2011).

Jo et al., "Surface modification using silanated poly(ethylene glycol)s," *Biomaterials*, 21:605-616 (2000).

Johnson et al., "Regulation of blood flow in single capillaries," *American Journal of Physiology*, 212:1405-1415 (1967).

Kaihara et al., "Silicon Micromachining to Tissue Engineer Branched Vascular Channels for Liver Fabrication," *Tissue Engineering*, 6(2):105-117 (2000).

Kiani et al., "Fluctuations in microvascular blood flow parameters caused by hemodynamic mechanisms," *American Journal of Physiology*, 266(5):H1822-H1828 (1994).

Kikuchi et al., "Modified Cell-Flow Microchannels in a Single-Crystal Silicon Substrate and Flow Behavior of Blood Cells," *Microvascular Research*, 47:126-139 (1994).

Koch et al., "Duration of Red-Cell Storage and Complications After Cardiac Surgery," *The New England Journal of Medicine*, 358:1229-1239 (2008).

Koch et al., "Peripheral blood leukocyte NO production and oxidative stress in multiple sclerosis,"*Multiple Sclerosis*, 14:159-165 (2008).

Krogh, "Studies on the physiology of capillaries. II. The reactions to local stimuli of the blood-vessels in the skin and web of the frog," *The Journal of Physiology*, 55:412-422 (1921).

Kuraoka, et al., "Ship-in-a-bottle synthesis of a cobalt phthalocyanine/porous glass composite membrane for oxygen separation," *Journal of Membrane Science*, 286(1-2):12-14 (2006).

Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).

Mazor et al., "Prolonged Storage of Red Cells: The Effect of pH, Adenine Phosphate," *Vox Sanguinis*, 66:264-269 (1994).

McDonald et al., "Poly(dimethylsiloxane) as a Material for Fabricating Microfluidic Devices," *Accounts of Chemical Research*, 35(7):491-499 (2002).

Meryman et al., "Extending the storage of red cells at 4° C.," *Transfus. Sci.*, 15(2):105-115 (1994).

Meryman et al., "Prolonged storage of red cells at 4° C.," *Transfusion*, 26(6):500-505 (1986).

Moll et al., "Dean vortices applied to membrane process. Part II: Numerical approach," *Journal of Membrane Science*, 288:321-335 (2007).

Moroff et al., "Proposed standardization of methods for determining the 24-hour survival of stored red cells," *Transfusion*, 24:109-114 (1984).

Murphy et al., "Increased Mortality, Postoperative Morbidity, and Cost After Red Blood Cell Transfusion in Patients Having Cardiac Surgery," *Circulation*, 116:2544-2552 (2007).

Ng et al., "Components for integrated poly(dimethylsiloxane) microfluidic systems," *Electrophoresis*, 23:3461-3473 (2002).

Ohkuma et al., "The preservative-exchange method using a sextuple-bag system for a 10-week storage period of red blood cells," *Transfusion Medicine*, 1:257-262 (1991).

Poxton, "Antibodies to lipopolysaccharide," *Journal of Immunological Methods*, 186:1-15 (1995).

Prefiltration before membrane filtration, hydrophobic, 25 µm 142 mm, retrieved on Aug. 26, 2014, from: www.emdmillipore.com/US/en/product/Prefiltration-before-membrane-filtration.

(56) References Cited

OTHER PUBLICATIONS

Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Supplementary European Search Report dated Jan. 20, 2015 in European Patent Application No. 12822378.2.
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old As-1 RBCs," *Transfusion*, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C. in additive solution (As-1, As-3, or As-5) for 42 days and then biochemically modified, frozen, thawed, washed, and stored at 4° C. in sodium chloride and glucose solution for 24 hours," *Transfusion*, 40:1341-1345 (2000).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of Trauma*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion*, 7(6):401-408 (1967).
Wu et al., "Polymer microchips bonded by $O_2$-plasma activation," *Electrophoresis*, 23:782-790 (2002).
Yoshida et al., "Anaerobic storage of red blood cells," *Blood Transfusion*, 8:220-236 (2010).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
Fage et al., "On transition from laminar to turbulent flow in the boundary layer," The gamma-ray transition of radio-bromine, *Proceedings of the Royal Society*, 178(973):205-227 (1940).
U.S. Appl. No. 10/295,781, filed Nov. 15, 2002, Bitensky et al.
U.S. Appl. No. 62/131,130, filed Mar. 15, 2015, Wolf et al.
U.S. Appl. No. 62/151,957, filed Apr. 23, 2015, Yoshida et al.
U.S. Appl. No. 12/901,350, filed Oct. 8, 2010, Yoshida et al.
Bensinger et al., "Prolonged maintenance of 2,3-DPG in liquid blood storage: Use of an internal Co.sub.2 trap to stabilize pH," *J. Lab. Clin. Med.*, 89(3):498-503 (1977).
Benson et al., "Accumulation of Pro-Cancer Cytokines in the Plasma Fraction of Stored Packed Red Cells," *J Gastrointest Surg.*, 16:460-468 (2012).
Buskirk et al., "Accumulation of Biologic Response Modifiers During Red Blood Cell Cold Storage," Transfusion, 49(Suppl3): 102A-103A (2009).
Chaplin et al., "The Proper Use of Previously Frozen Blood Cells for Transfusion," Blood, 59:1118-1120 (1982).
Cognasse et al., "The role of microparticles in inflammation and transfusion: A concise review," Transfus. Apher. Sci. 53(2):159-167 (2015).
De Korte et al., "Prolonged maintenance of 2,3-diphosphoglycerate acid and adenosine triphosphate in red blood cells during storage," Transfusion, 48:1081-1089 (2008).
Dumont et al., "CO2-dependent metabolic modulation in red cells stored under anaerobic conditions," Transfusio 56(2): 392-403 (2016)(epub 2015).
Extended European Search Report dated Jun. 15, 2015, in European Patent Application No. 11820660.6.
Fatouros et al., "Recombinant factor VII SQ—influence of oxygen, metal ions, pH and ionic strength on its stability in aqueous solution," International Journal of Pharmaceutics, 155(1):121-131 (1997).
"Friction Factor for Flow in Coils and Curved Pipe," Neutrium Available on the world wide web at neutrium.net/fluid_flow/friction-factor-for-flow-in-coils-and-curved-pipe/. (2017).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Heaton et al., "Use of Adsol preservation solution for prolonged storage of low viscosity As-1 red blood cells," Br J. Haematol, 57(3):467-478 (1984).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Högman, "Preparation and Preservation of Red Cells," Vox Sanguinis 74(Suppl. 2):177-187 (1998).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Preliminary Report on Patentability completed on Oct. 18, 2011, in International Patent Application No. PCT/US2010/031055.
International Search Report completed on Dec. 21, 2011, in International Patent Application No. PCT/US11/49168.
International Search Report for PCT/US2016/021794 dated Jul. 18, 2016.
Irsch et al., "Pathogen inactivation of platelet and plasma blood components for transfusion using the Intercept Blood SystemTM," *Transfusion Medicine and Hemotherapy*, 38:19-31 (2011).
Jarus et al., "Barrier Properties of polypropylene/polyamide blends produced by microlayer coextrusion," Polymer 43:2401-2408 (2002).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kilkson et al., "Platelet metabolism during storage of platelet concentrates at 22°C.," Blood 64(2):406-414 (1984).

(56) References Cited

OTHER PUBLICATIONS

Kynar Flex Product Catalog, downloaded May 20, 2015 from Kynar.com.
Lowndes, "Blood Interference in fluorescence spectrum: Experiment, analysis and comparison with intraoperative measurements on brain tumor," *Bachelor Thesis*, Linköpping University, pp. 1-42 (2010).
Lundblad, "Factor VIII—Reducing agents, copper ions, and stability," http://lundbladbiotech.com.
Moroff et al., "Factors Influencing Changes in pH during Storage of Platelet Concentrates at 20-24° C.," Vox Sanguinis, 42(1):33-45 (1982).
Moroff et al., "Concepts about current conditions for the preparation and storage of platelets," *Transfus Med Rev* V(1):48-59 (1991).
Murphy et al., "Platelet storage at 22° C.: role of gas transport across plastic containers in maintenance of viability," *Blood* 46(2):209-218 (1975).
Musante et al., "Active Focal Segmental Glomerulosclerosis is Associated with Massive Oxidation of Plasma Albumin," Journal of the American Society of Nephrology, 18(3):799-810 (2007).
Parkkinen et al., "Plasma ascorbate protects coagulation factors against photooxidation," *Thromb Haemost* 75(2):292-297 (1996).
Picker et al., "Current methods for the reduction of blood-borne pathogens: a comprehensive literature review," *Blood Transfusion* 11:343-348 (2013).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Ramstack et al., "Shear-induced activation of platelets," *J. Biomech.*, 12:113-125 (1979).

Reynolds et al., "S-nitrosohemoglobin deficiency: a mechanism for loss of physiological activity in banked blood," *Proceedings of the National Academy of Sciences*, 104(43):17058-17062 (2007).
Rock et al., "Nutricel as an additive solution for neonatal transfusion," *Transfusion Science*, 20:29-36 (1999).
Schubert et al., "Whole blood treated with riboflavin and ultraviolet light: Quality assessment of all blood components produced by the buffy coat method," *Transfusion* 55(4):815-823 (2014).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Su et al., "Impermeable barrier films and protective coatings based on reduced graphene oxide," Nature Communications 5 Article No. :4843 (2014).
Sutera et al., "Deformation and Fragmentation of Human Red Blood Cells in Turbulent Shear Flow," Biophys. J., 15:1-10 (1975).
"Transition and Turbulence," https://www.princeton.edu/~asmits/Bicycle_web/transition.html . Adapted from The Engine and the Atmosphere: An Introduction to Engineering by Z. Warhaft, Cambridge University Press, (1997).
Wallvik et al., "Platelet Concentrates Stored at 22° C. Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Yazer et al., "Coagulation factor levels in plasma frozen within 24 hours of phlebotomy over 5 days of storage at 1 to 6° C.," *Transfusion*, 48:2525-2530 (2008).
Yoshida et al., "Extended storage of red blood cells under anaerobic conditions," *Vox Sanguinis*, 92:22-31 (2007).
Zimring et al., "Established and theoretical factors to consider in assessing the red cell storage lesion," Blood, 125:2185-2190 (2015).

\* cited by examiner

METHOD AND SYSTEM FOR REMOVING OXYGEN AND CARBON DIOXIDE DURING RED CELL BLOOD PROCESSING USING AN INERT CARRIER GAS AND MANIFOLD ASSEMBLY

CROSS-REFERENCE TO RELATED APPLICATION

This application is a continuation of U.S. application Ser. No. 13/432,810 filed on Mar. 28, 2012 (pending), which claims benefit of U.S. Provisional Application Ser. No. 61/468,377 filed on Mar. 28, 2011 (expired), the contents of which are incorporated by reference herein in their entireties.

BACKGROUND OF THE INVENTION

1. Field of the Invention

The present disclosure relates to a portable blood treatment manifold assembly. More, particularly, the present disclosure relates to a portable blood treatment manifold assembly for leukoreduction and oxygen and/or carbon dioxide depletion of blood in preparation for blood storage and/or transfusion to a recipient.

2. Background of the Art

The supplies of liquid blood in are currently limited by storage systems used in conventional blood storage practice. Using current systems, stored blood expires after about 42 days of refrigerated storage at a temperature above freezing (i.e.1-6° C.) as packed blood cell preparations. Red blood cells (RBCs) may be concentrated from whole blood with separation of the liquid blood component (plasma). Expired blood cannot be used and is discarded.

There are periodic shortages of blood that occur due to donation fluctuation, emergencies and other factors. The logistics of blood supply and distribution impact the military, especially during times of combat and remote hospitals or medical facilities making blood processing or transfusions very difficult. Accordingly, there is a need to be able to rapidly prepare RBCs for storage or for transfusions in remote locations.

Storage of frozen blood is known in the art but such frozen blood has limitations. For a number of years, frozen blood has been used by blood banks and the military for certain high-demand and rare types of blood. However, frozen blood is difficult to handle. It must be thawed which makes it impractical for emergency situations. Once blood is thawed, it must be used within 24 hours. U.S. Pat. No. 6,413,713 to Serebrennikov is directed to a method of storing blood at temperatures below 0° C.

U.S. Pat. No. 4,769,318 to Hamasaki et al. and U.S. Pat. No. 4,880,786 to Sasakawa et al. are directed to additive solutions for blood preservation and activation. U.S. Pat. No. 5,624,794 to Bitensky et al., U.S. Pat. No. 6,162,396 to Bitensky et al., and U.S. Pat. No. 5,476,764 are directed to the storage of red blood cells under oxygen-depleted conditions. U.S. Pat. No. 5,789,151 to Bitensky et al is directed to blood storage additive solutions.

Additive solutions for blood preservation and activation are known in the art. For example, Rejuvesol (available from enCyte Corp., Braintree, Mass.) is add to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells.

In light of current technology, there is a need for a portable and cost effective apparatus and methodology for the preparation of RBCs that removes leukocytes and oxygen and/or carbon dioxide in advance of transfusion or in preparation for anaerobic storage.

SUMMARY OF THE INVENTION

Accordingly, the present disclosure provides a system that is capable of removing oxygen and/or carbon dioxide and/or leukocytes from RBCs in advance of transfusion or for further storage in an anaerobic environment.

The present disclosure also provides for a system and methodology for the preparation of RBCs in advance of transfusion or for further storage in an anaerobic environment.

It is a further object of the present disclosure to provide a stand-alone portable system that has an oxygen or an oxygen/carbon dioxide depletion (OCDD) device that removes oxygen or oxygen and or carbon dioxide from RBCs passing through the device. The OCDD device operates with a gas exchange system that pumps gas into the device through which RBCs that first passes through an oxygen or oxygen/carbon dioxide (OCDD) device to remove oxygen or oxygen/carbon dioxide from such RBCs. The RBCs are thereby depleted of oxygen or oxygen/carbon dioxide and deposited in a blood storage bag for extended storage or storage in advance of transfusion.

It is a still further object of the present disclosure to provide a stand alone portable system that pumps gas into the device through which RBCs pas through a leukoreduction filter and an oxygen and/or carbon dioxide (OCDD) device to remove leukocytes and oxygen or oxygen/carbon dioxide from such RBCs, respectively. The RBCs are thereby free of leukocytes and depleted of oxygen or oxygen/carbon dioxide and deposited in a blood storage bag for extended storage or storage in advance of transfusion.

It is still a further object of the present disclosure to provide a standalone portable system that circulates oxygen depleted and or/carbon dioxide adjusted air air or inert gas mixtures through an OCDD device to remove such gases from RBCs flowing through the filter in preparation for anaerobic storage or transfusion. Such system contains oxygen, carbon dioxide and/or partial pressure sensors between an inlet manifold that receives oxygen and/or carbon dioxide rich air or inert gas from an OCDD device and an outlet manifold. The sensors monitor and regulate oxygen and or carbon dioxide levels in air or inert gas mixtures received in the outlet manifold and monitor oxygen and carbon dioxide partial pressure of filtered gas that is pumped pumped back to OCDD device.

It is still a further object of the present disclosure to provide a standalone portable system that reduces leukocytes and circulates oxygen and/or carbon dioxide adjusted air or inert gas mixtures through an OCDD device to remove such gases from RBCs in preparation for anaerobic storage or transfusion. Such system contains oxygen, carbon dioxide and/or partial pressure sensors between an inlet manifold that receives oxygen and/or carbon dioxide rich air or inert gas mixtures from an OCDD device and an outlet manifold that feeds oxygen and carbon dioxide depleted air or inert gas mixtures back is to the OCDD device. The sensors monitor and regulate oxygen and or carbon dioxide levels in gas received in the outlet manifold and monitor oxygen and carbon dioxide partial pressure of gas that is pumped back to OCDD device.

A portable assembly for processing red blood cells RBCs including a disposable blood collection set including a blood bag, an anaerobic storage bag and an oxygen and/or oxygen and carbon dioxide depletion device disposed between the blood collection bag and anaerobic storage bag. The portable assembly further provides for a gas circulation device in fluid communication with the oxygen or oxygen and carbon dioxide depletion device, The gas circulation device includes a pressure source that is able circulate flushing gas through the depletion device as RBCs pass from the blood collection bag, through the depletion device and into the anaerobic storage bag.

A portable assembly for processing red blood cells (RBCs) including an oxygen or oxygen and carbon dioxide depletion (OCDD) device. The OCDD device includes a cartridge having an inlet and an outlet and a plurality of hollow fibers disposed between the inlet and the outlet for transporting RBCs through the OCDD device. The plurality of hollow fibers are surrounded by a continuous space. The portable assembly includes a gas exchange device in fluid communication with the OCDD device. The gas exchange device includes a pressure source that is able to circulate a flushing gas through the continuous space and remove oxygen and/or carbon dioxide from RBCs passing through the OCDD device.

These and other objects and advantages of the present invention and equivalents thereof, are achieved by the methods and compositions of the present invention described herein and manifest in the appended claims.

BRIEF DESCRIPTION OF THE DRAWINGS

FIG. 2d illustrates an OCDD device of the embodiment of FIG. 1a;

DETAILED DESCRIPTION OF THE DISCLOSURE

Figure 1A:
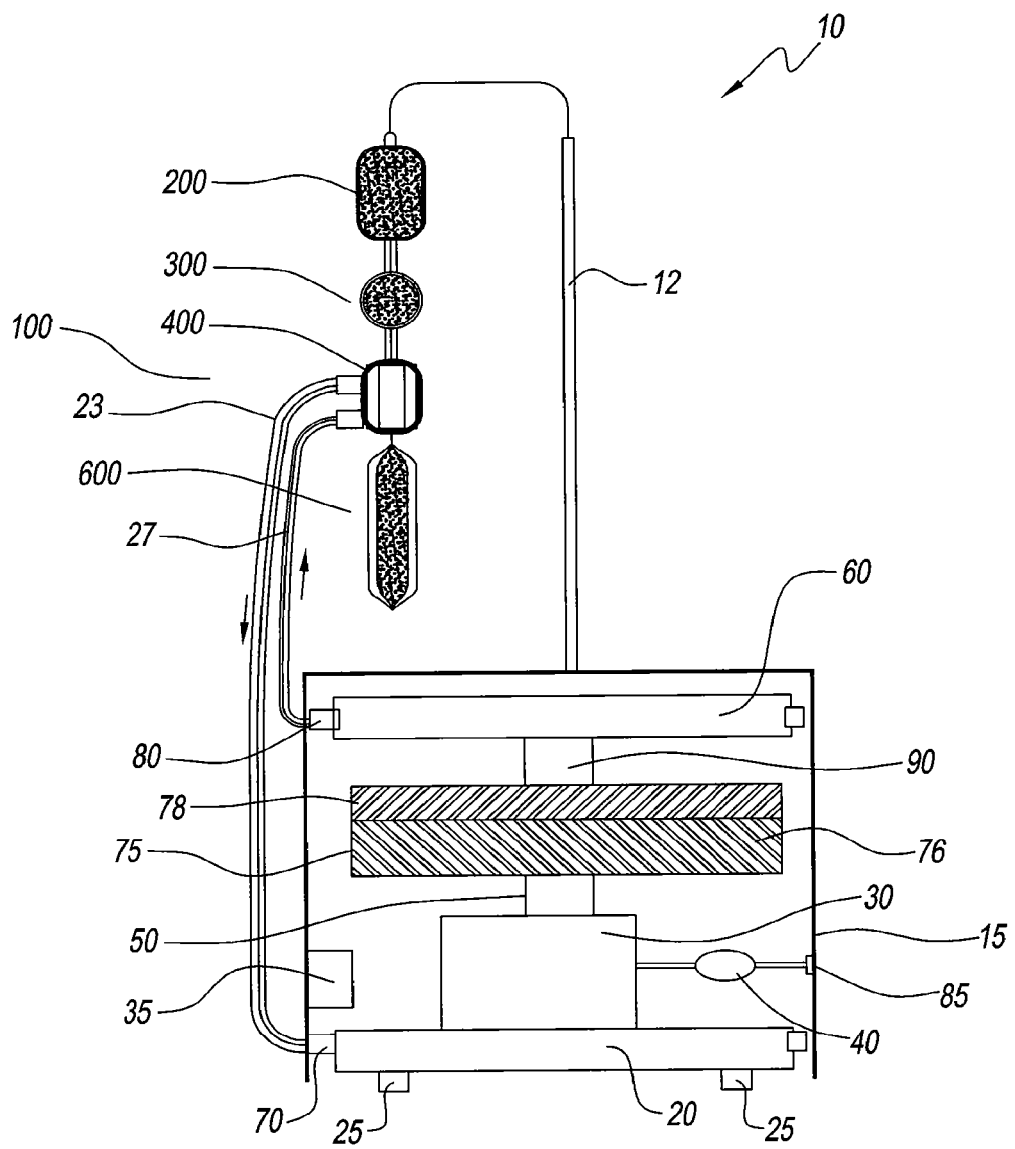
FIG. 1a illustrates a portable blood processing system according to the present disclosure.

Referring to FIG. 1, a stand alone blood processing system is shown and referenced using reference numeral 10. System 10 includes a housing 15 and supports a blood collection and depletion system 100 (hereinafter "collection system 100").

Collection system 100 includes a blood bag 200, a leukoreduction filter 300, an oxygen and/or carbon dioxide depletion (OCDD) device 400 and an anaerobic storage bag 600. Device 400 is able to deplete oxygen or alternatively, oxygen and carbon dioxide from gas from RBCs. Collection system 100 is suspended within system 10 to enable convenient movement and transport of blood preparation processes in locations that may be remote from a standard hospital or clinical setting. The orientation of system 100, permits RBCs in blood bag 200 to flow under the force of gravity to anaerobic storage bag 600. Although a single collection system 100 is shown, stand 12 of housing 15 could carry as many as ten or more such systems for processing. Housing 15 includes a gas circulation device including a pressure source such as a pump 30 or a vacuum or a pressurized container, a valve/pressure regulator 40 and further components that will be discussed further that enable gas to circulate and pass through OCDD device 400. Inlet 410 and outlet 415 (FIG. 2d) that area connected to tubing 427 and 426, respectively.

Collection system 100 includes a blood bag 200 that contains RBCs that have been collected from whole blood. Generally, whole blood is collected from a donor using traditional methods and processed using centrifugation to separate plasma and RBCs. Blood bag 200 is a standard blood collection bag. RBCs are collected in a blood bag 200 that may contain an additive. An additive solution, such as, for example, OFAS3, includes adenine, dextrose, mannitol, $NaH_2PO_4$, and optionally NaCl and/or $NH_4Cl$. Additive solution OFAS3 preferably comprises ingredients having the following ranges: about 0.5-4.0 mmole/liter of adenine, about 50-150 mmole/liter of dextrose, about 20-70 mmole/liter of mannitol, about 0-100 mmole/liter of NaCl, about 2-20 mmole/liter of $NaH_2PO_4$, and about 0-30 mmole/liter $NH_4Cl$. Preferably, OFAS3, has an adjusted pH from about 5.5-7.5 and includes about 2 mmole/liter adenine, about 110 mmole/liter dextrose, about 55 mmole/liter NaCl, and about 12 mmole/liter $NaH_2PO_4$ and an adjusted pH of about 6.5. Additives such as SAGM, PAGG-SM, AS-1, AS-3, AS-5, SOLX, MAPS, PAGG-GM or any additive approved for blood storage may also be used in this system.

RBCs contained in blood bag 200 flow under the force of gravity to leukoreduction filter 300 and through OCDD device 400. Leukoreduction is the process of removing white blood cells from the whole blood or RBCs. Leukocytes in blood products can cause immunosuppressive effects and can pre-dispose patients to an increased risk of viruses, fevers, and have deleterious effects on RBCs.

Leukoreduction reduces RBC storage lesions, reduces primary alloimunization and reduces total number of transfusion reactions.

The process of leukoreducing RBCs preferably occurs after the RBCs have been separated from the plasma and can occur before or after removal of oxygen and carbon dioxide have been removed from the RBCs. In either case, leukoreduction should occur before storage of RBCs and anaerobic storage bag 600.

Figure 2A:
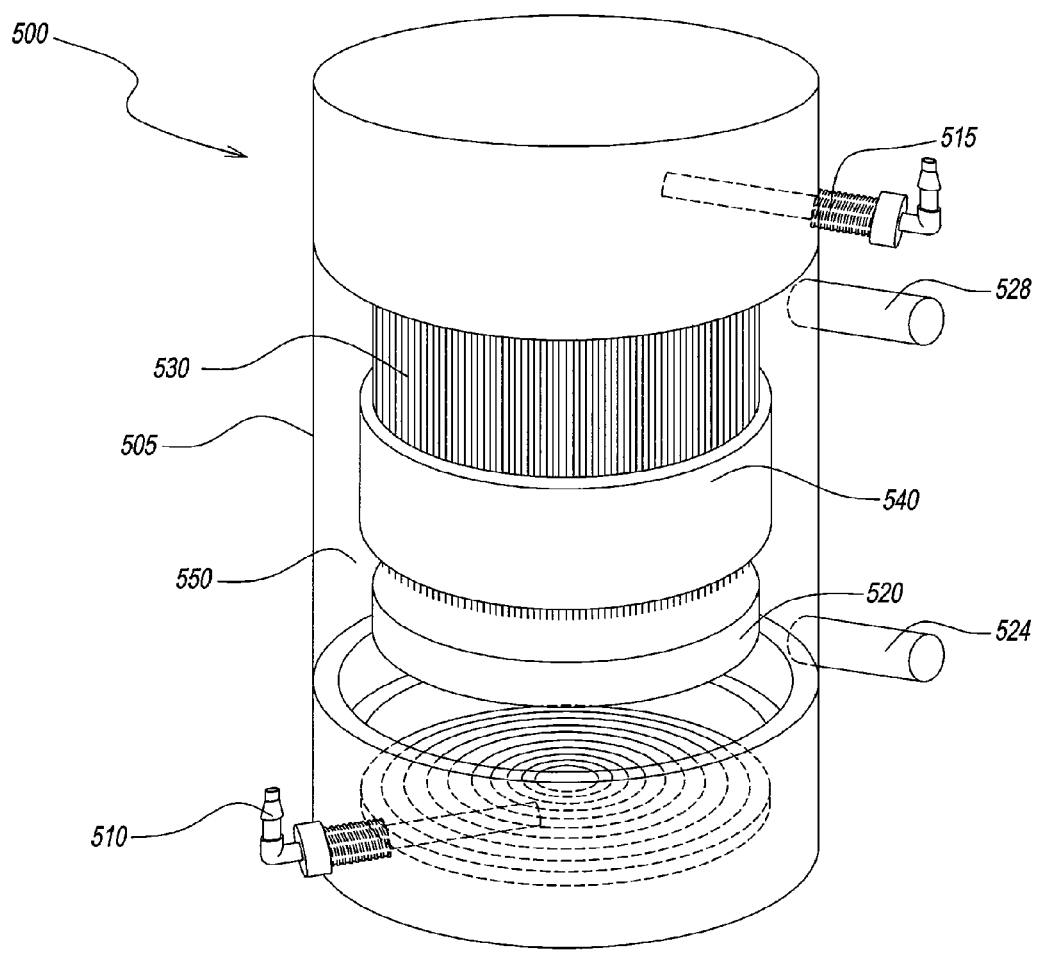
FIGS. 2a through 2c illustrate a leukoreduction filter incorporated into an OCDD device according to the embodiment of FIG. 1e.
Figure 2B:
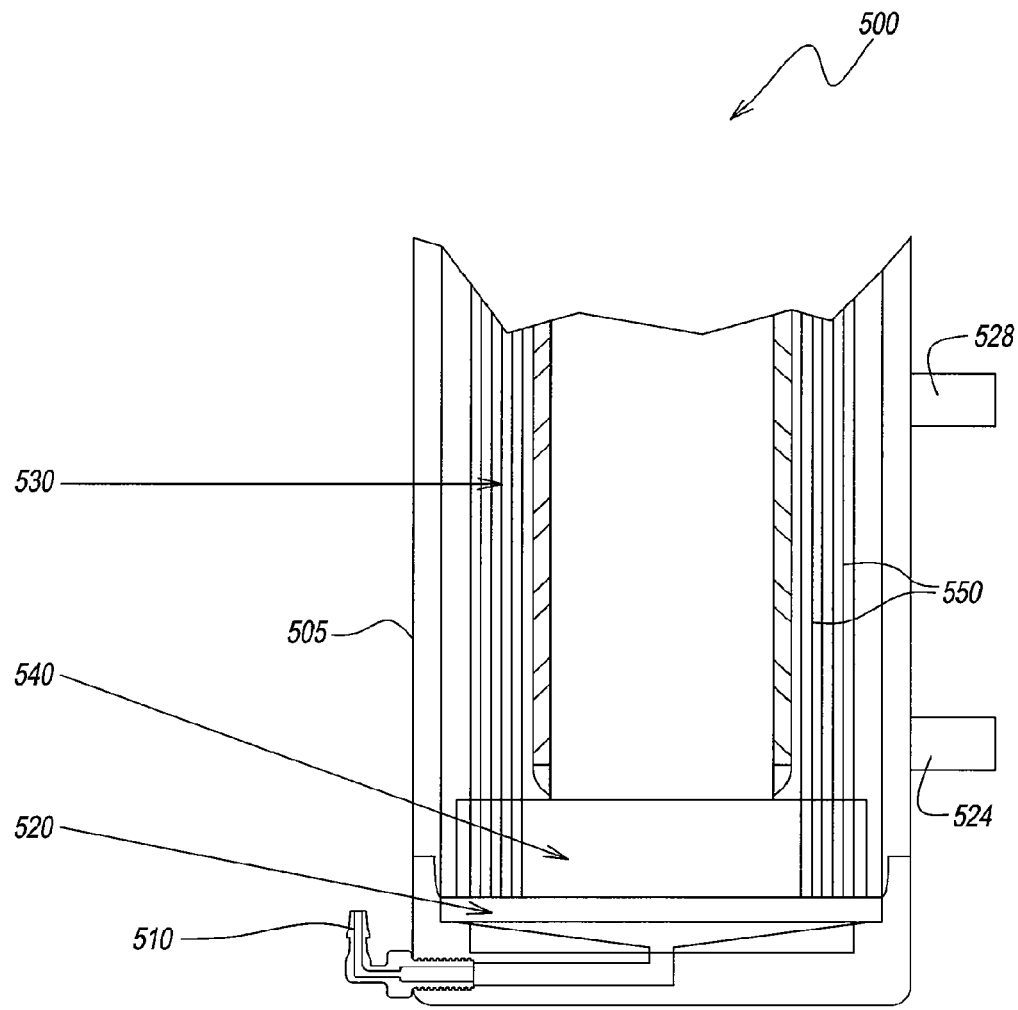
Figure 2D:
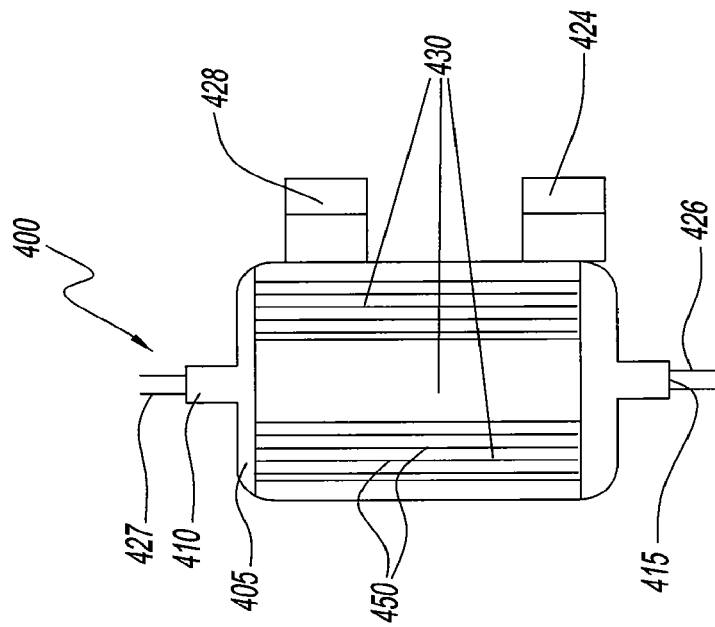
Figure 2C:
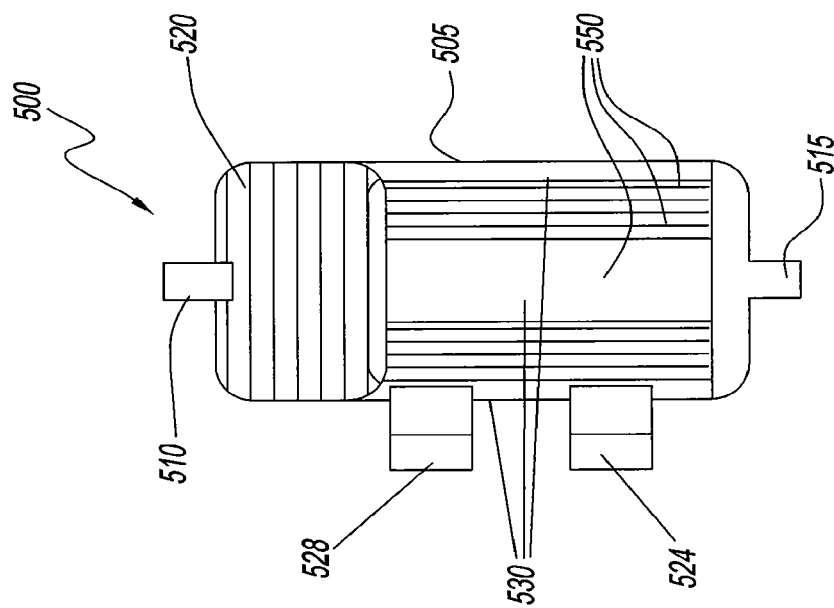

Referring to FIGS. 2a, 2b, and 2c leukoreduction filter 300 is incorporated into OCDD device 500. OCDD device 500 includes a cartridge 505, an inlet 510, a leukoreduction filter 520, a plurality of hollow fibers 530, and a fiber support 540 to hold the plurality of hollow fibers 530. OCDD device 500 also includes an outlet 515 for passage of RBCs. Leukoreduction filter 520 is preferably a fibrous or a felt-like filtering material that captures leukocytes, prior to such leukocytes travelling through plurality of hollow fibers 530. Fiber support 540 supports the plurality of hollow fibers 530 in a vertical configuration and may be made from a material such as polyurethane or a similar material. Either whole blood or pRBC flow through filter 520 during leukoreduction process. OCDD device 500 is in communication with gas from pump 30 via an inlet 524 and an outlet 528.

OCDD cartridge 500 contains approximately 5000 fibers for the passage of RBCs. More or fewer fibers may be used to generate a sufficient surface area for gas exchange to reduce the oxygen and/or carbon dioxide concentrations to the desired levels. Plurality of hollow fibers 530 are for the purpose of removing oxygen or oxygen and carbon dioxide from RBC and will be discussed further below. Gas spaces 550, outside of hollow fibers and inside of cartridge 505, that surround plurality of hollow fibers 530 and are filled with a carrier gas. Gas permeable material or porous materials of plurality of hollow fibers 530 enable oxygen and carbon dioxide to pass from RBCs to carrier gas when such gas is circulated through OCDD device 500. OCDD device 500 depletes, $O_2$ and $CO_2$, or $O_2$, or $CO_2$ alone, or $O_2$ with specific levels of $CO_2$ by supplying an appropriate composition of flushing gas. Gases appropriate for depletion for use in OCDD devices are any inert gasses that will not cause harm to the RBCs or blood recipient, for example, Ar, He, $N_2$, $Ar/CO_2$, $He/CO_2$ or $N_2/CO_2$.

RBCs flow into OCDD device 500 to be depleted of oxygen or oxygen and carbon dioxide. OCDD device 500 reduces the degree of RBC hemoglobin oxygen saturation levels to less than 3% and the carbon dioxide partial pressure to less than 50 Torr at 37° C. OCDD device 500 is a combination oxygen and carbon dioxide filter that removes oxygen and carbon dioxide from RBCs to enhance the storage life of such RBCs and promotes optimal transfusion. OCDD device 500 is used with housing 115 and stand 12 of FIG. 1e and contains same components as embodiment of FIG. 1a.

Alternatively, as shown in FIG. 2d, an OCDD device 400 does not contain the leukoreduction capability and is only capable of depleting oxygen or oxygen and carbon dioxide from RBCs passing there through. FIG. 2d illustrates an OCDD device 400 that has an inlet 410 for the entry of RBCs, an outlet 415 for the passage of RBCs, and a plurality of fibers 430 through which such RBCs pass to be deleted of oxygen and/or carbon dioxide gas. OCDD device 400 also contains an entry port 424 for flushing gas and an exit port 428 for the egress of flushing gas and a plurality of spaces 450 that surround plurality of fibers 430 that are inside of cartridge 405 and where gas exchange from RBCs to flushing gas occurs. The circulation of gas through OCDD device 400 via entry port 424, exit port 428 and plurality of spaces 450 ensures that the partial pressure of oxygen and carbon dioxide in RBCs stored in bags 600 is at acceptable levels for optimal storage of RBCs.

Referring to FIG. 1a, again, housing 15 includes an inlet manifold 20, a pump 30, an outlet manifold 60 and an inlet valve/pressure regulator 40. OCDD cartridge 400 is connected to inlet manifold 20 and outlet manifold 60 by tubing 27 and 13 or direct connections 128 and 124 (FIG. 1c) respectively. A first oxygen/carbon dioxide sensor 50 and a second oxygen/carbon dioxide sensor 90 are disposed between inlet manifold 20 and outlet manifold 60. System 10 is connectable to an AC outlet or other supply of power for operation of pump 30. Alternatively, system 10 can connect to a battery for remote operation of system 10.

Housing 15 contains a disposable or re-usable sorbent cartridge 75 that is disposed between inlet manifold 20 and outlet manifold 60 to purify and air or inert gas mixture that has passed through OCDD device 400. Sorbent cartridge 75 is a large cartridge that is preferably iron based or other inorganic and/or organic compound that can physically or chemically absorb oxygen or oxygen/carbon dioxide. Sorbent cartridge 75 contains an oxygen and/or a carbon dioxide sorbent 76. As an alternative to a large sorbent pack or organic and inorganic compounds, oxygen and carbon dioxide can also be depleted from oxygen and carbon dioxide rich air or inert gas mixture by using membrane filters designed for gas separation, such as those found in nitrogen generator systems. In addition to oxygen or oxygen/carbon dioxide sorbent 76, sorbent cartridge 75 also includes activated charcoal filter 78 to absorb volatiles produced by oxygen or oxygen/carbon dioxide sorbent. Charcoal filter 78 also includes a HEPA filter to remove any particulates.

System 10 also includes various sterilization filter sensor assemblies 70, 80 and 85. Sterilization filter sensor assembly 70 are dispose between tubing 23 and inlet manifold 20. Sterilization filter sensor assembly 80 is disposed between outlet manifold 60 and tubing 27. Filters 70 and 80 capture any pathogens and/or particulates that could enter gas flow between respective tubing and manifold and compromise filtration and or purification of RBCs. Filters in 70 and 80 filter sensor assemblies monitor levels partial pressures of oxygen and carbon dioxide for an individual OCDD 400 (or 500). Sterilization filter 85 is disposed between external portion of housing 15 and inlet valve pressure regulator 40. Sterilization filter filter sensor assembly 85 monitors gas entering pump 30. Filter in filter sensor assembly 85 capture pathogens and particulates between system 10 and ambient air or inert gas mixture and are also able to sense levels of oxygen, carbon dioxide, temperature and pressure and humidity. Filter sensor assemblies 70, 80 and 85 also function as sensors and are in communication with controller 35. Controller 35 is programmed with predetermined set points to monitor and control concentration and flow rate of oxygen and carbon dioxide, temperature, humidity and total pressure of the gas mixtures. Should levels not be appropriate, a warning signal, such as a light or alarm, informs an operator that sorbent cartridge, sterilization filter or HEPA filter should be replaced.

Housing 15 includes casters 25 to permit movement and positioning of system 10. System 10 also includes a large sorbent cartridge 75 or hollow fiber gas separation module.

In operation, and as shown in FIG. 1, RBCs flow from collection bag 200 into OCDD cartridge directly or via leukoreduction filter. Flushing gas is simultaneously circulated through OCDD cartridge 400. The flow of oxygen or oxygen/carbon dioxide adjusted gas and oxygen/carbon dioxide rich gas to and from OCDD cartridge 400 is carried by tube 27 and tube 23, respectively. Tube 23 is connected to inlet manifold 20 and tube 27 is connected to outlet manifold 60. Tube 23 is connected to inlet manifold by a sterilization filter sensor assembly 70. Similarly, outlet manifold 60 is connected to tube 27 by sterilization filter 80.

After oxygen rich air or inert gas mixture egressing from OCDD device 400 via tubing 23, such air or inert gas mixture is received at inlet manifold 20, and pumped via pump 30 through sensor 50. Pump 30 operates to maintain gas flow through system 10. Pump 30 is preferably an electrically driven pump that regulates pressures and flows. Pump 30 is connected to a valve 40, preferably a one way valve and pressure regulator that accepts ambient air or inert gas mixture at ambient pressure or insert gasses at elevated pressures. Sensor 50 and sensor 90 measure partial pressure of oxygen and carbon dioxide, in addition to gas partial pressure, temperature, flowrate total pressure and humidity of the entire portable assembly. Air or inert gas is purified in cartridge 75 and returned to OCDD 400 to continue to depletion RBCs before such RBCs flow into anaerobic storage bag 600.

Figure 1B:
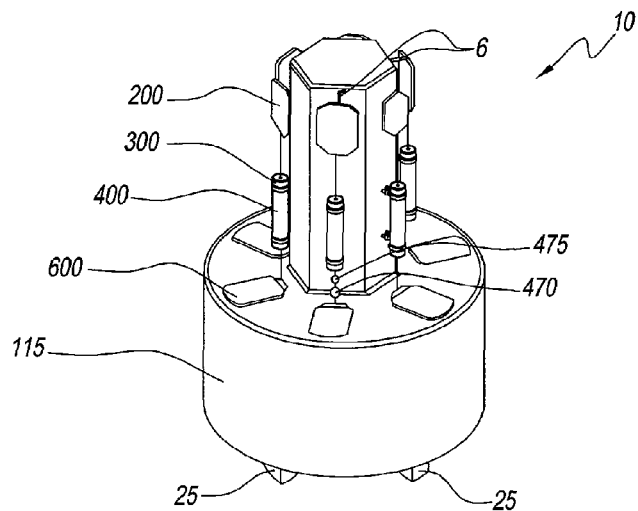
FIG. 1b illustrates an alternative embodiment of the present disclosure in which red blood cells are processed using a load cell.
Figure 1C:
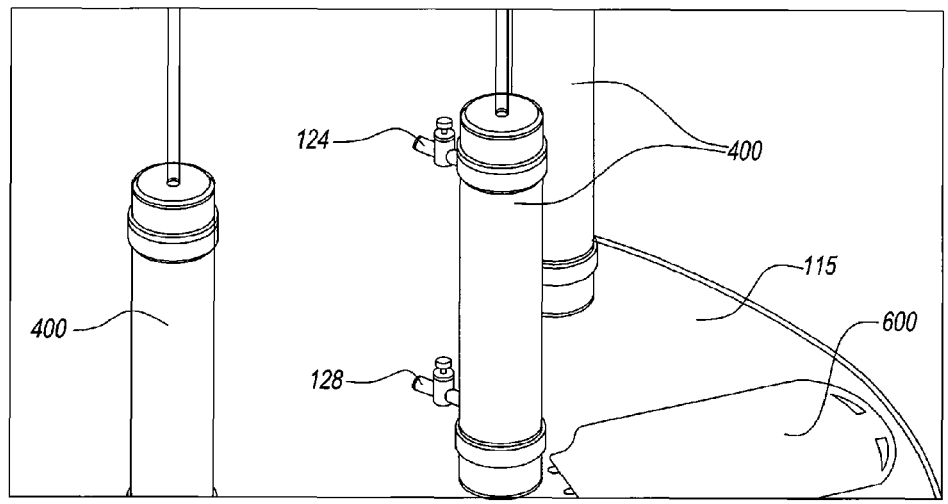
FIG. 1c illustrates the OCDD device of the embodiment of FIG. 1b directly connected to the processing system.
Figure 1D:
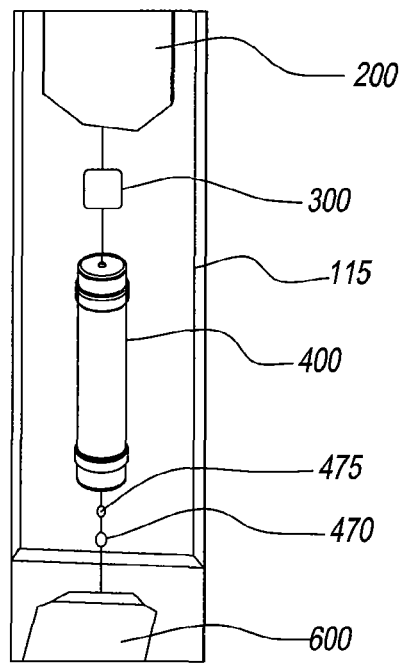
FIG. 1d illustrates a collection system that incorporates a flow regulator according to the embodiment of FIG. 1b.
Figure 1E:
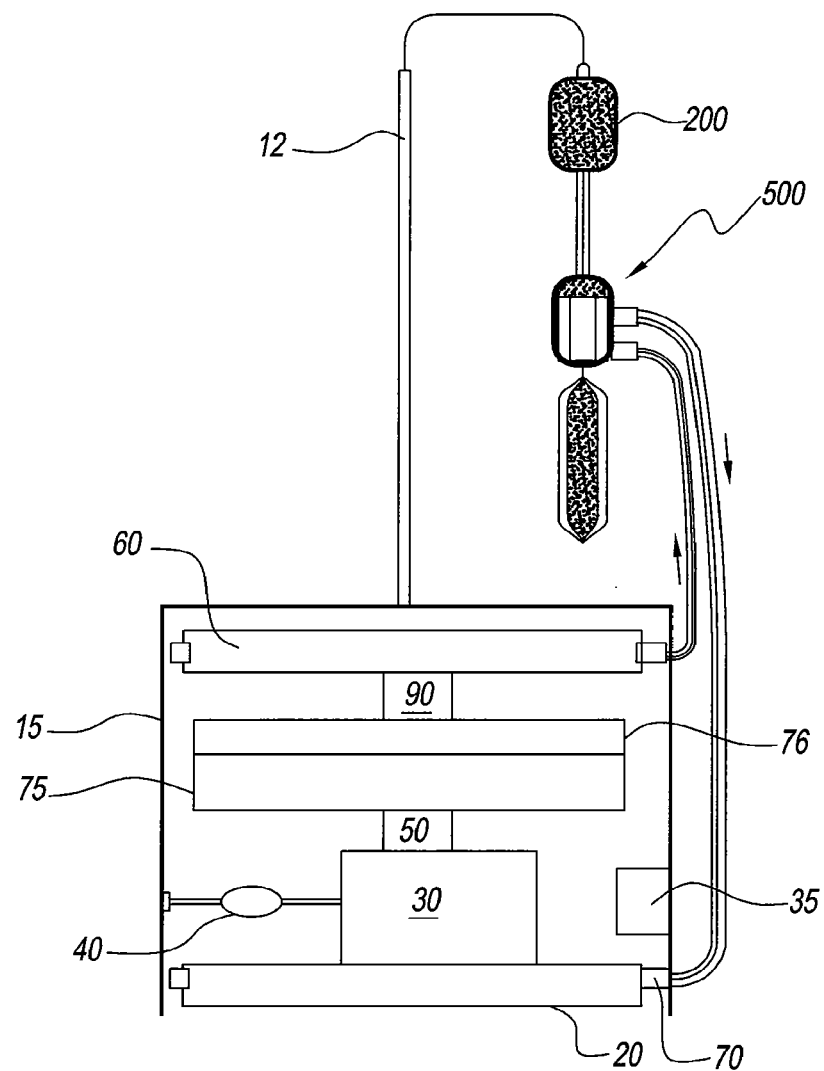
FIG. 1e illustrates a collection system that incorporates a leukoreduction filter with an OCDD device.

FIGS. 1b through 1d show an alternative embodiment of a housing 115. Housing 115 contains similar gas exchange components as housing 15. Namely, housing 115 also contains an inlet manifold 20, a pump 30, an outlet manifold 60 and an inlet valve/pressure regulator 40 contained within housing 115. Housing 115 also contains a load cell 6 that is connected to bag 200 and a flow regulator valve 470. Load cell 6 measures the unit weight in bag 200 and communicates change in mass in bag to a controller 35 that communicates with flow regulator valve 470 to monitor flow of RBCs through OCDD device 400. By monitoring change of mass of RBCs in bag 200, valve 470 can be adjusted to ensure that RBCs remain in OCDD device 400 for adequate oxygen or oxygen and carbon dioxide removal. Controller 35 is in electrical communication with load cell 6, flow regulator valve 470 and oxygen saturation sensor 475. Oxygen saturation sensor 475 measures oxygen saturation levels in RBCs. Controller 35 receives signals indicative of oxygen saturation levels and in turn sends signal to adjust flow regulator valve 470 o assure adequate oxygen depletion levels in RBCs. The several bags 200 (FIG. 1b) can be connected to housing 115 and be similarly equipped with a flow regulator valve 470 although only one flow regulator 470 is shown. Housing 115 has an outside surface to which OCCD devices 400 can be directly connected via couplings. By configuring OCDD devices 400, as shown in FIGS. 1b through 1d, so that they are directly connected to housing 115 via couplings 124 and 128, the need for tubing of the embodiment of FIG. 1a is eliminated. The configuration of housing 115 can also be used with devices 500 that include leukoreduction capability.

Figure 3:
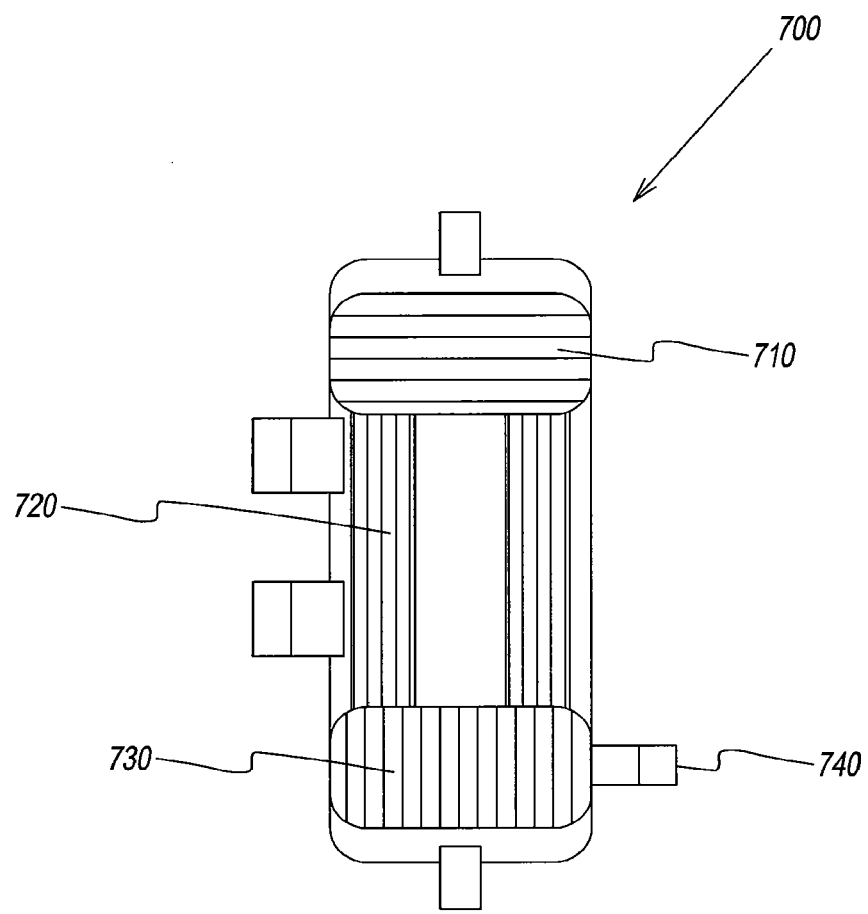
FIG. 3 illustrates an OCDD device according to a further embodiment of the present disclosure having OCCD device, leukoreduction filter and plasma separation device in a unitary structure.

Referring to FIG. 3, a multifunction OCDD device 700 is a combination leukoreduction filter 710, OCDD device 720, in combination with a plasma separator 730. Multifunction OCDD device 700 eliminates the need for separation of the whole blood, received from donor, which is currently a separated by using a centrifuge. By combining these three devices into a single device, the need for a separate centrifuge, a highly costly and cumbersome device, is eliminated. This embodiment contains a leukreduction portion 710, a OCDD device 720 and a plasma separator 730. Plasma flows through port 740 to a further collection bag for further processing. Accordingly, in this embodiment, whole blood can be collected from a donor, leukocytes can be removed, oxygen, or oxygen and carbon dioxide can be removed and plasma and platelets can be removed to pass RBCs through device. The RBCs are then deposited into collection bag 600 for storage or transfusion to a recipient. Multifunction OCDD 700 as part of collection system 100 and system 10 permit rapid transformation of whole blood to stored RBCs for immediate storage or transfusion to a recipient.

Although the present disclosure describes in detail certain embodiments, it is understood that variations and modifications exist known to those skilled in the art that are within the disclosure. Accordingly, the present disclosure is intended to encompass all such alternatives, modifications and variations that are within the scope of the disclosure as set forth in the disclosure.

We claim:

1. A method of processing red blood cells (RBCs) comprising:
   filtering a flushing gas source through a gas circulation device to generate sterile flushing gas, said gas circulation device comprising, in fluid communication with each other:
      a flushing gas source providing said flushing gas;
      a gas outlet manifold;
      a first gas sterilization filter;
      a second gas sterilization filter;
      one or more gas sensor assemblies;
      a gas inlet manifold; and
      a controller,
      wherein said one or more gas sensor assemblies are selected from the group consisting of an oxygen sensor, an oxygen partial pressure sensor, a carbon dioxide sensor, a carbon dioxide partial pressure sensor, and combinations thereof;
   providing said sterile flushing gas to an oxygen or oxygen and carbon dioxide depletion (OCDD) device; and
   flowing said RBCs through said OCDD device to remove oxygen or oxygen and carbon dioxide from said RBCs, producing oxygen or oxygen and carbon dioxide reduced red blood cells.

2. The method according to claim 1, wherein said gas circulation device is contained in a housing comprising a sorbent disposed between said flushing gas source and said gas outlet manifold, and said method further comprises removing oxygen or oxygen and carbon dioxide from said flushing gas.

3. The method according to claim 2, further comprising determining levels of oxygen or carbon dioxide in said flushing gas, wherein said one or more gas sensor assemblies comprises a first gas sensor assembly comprising a first partial pressure sensor disposed between said flushing gas source and said sorbent, and a second gas sensor assembly comprising a second partial pressure sensor disposed between said sorbent and said gas outlet manifold.

4. The method according to claim 1, wherein said gas circulation device further comprises one or more load cells in communication with said controller to regulate one or more flow regulator valves, and said method further comprises measuring the load of unprocessed RBCs, and controlling said flowing.

5. The method according to claim 4, wherein said controller detects a signal from said one or more load cells and then communicates a signal to restrict or facilitate a flow of RBCs through said one or more flow regulator valves.

6. The method according to claim 1, wherein said one or more gas sensor assemblies comprises an oxygen sensor in communication with said controller to regulate one or more flow valves, and said method further comprises measuring the level of oxygen saturation in said RBCs flowing through said OCDD device.

7. The method according to claim 6, wherein said controller detects a signal from said oxygen sensor and then communicates a signal to restrict or facilitate a flow of RBCs through said one or more flow regulator valves.

8. The method according to claim 1, wherein said flushing gas comprises Ar, He, $N_2$, Ar/$CO_2$, He/$CO_2$, $N_2$/$CO_2$, a combination of inert gasses, or any combination of inert gasses and $CO_2$.

9. The method according to claim 1, wherein said flushing gas source is selected from the group consisting of a pump, a vacuum, and a pressurized container.

10. The method according to claim 1, further comprising depositing said oxygen or oxygen and carbon dioxide reduced red blood cells in a blood storage bag.

11. The method according to claim 1, further comprising adding an additive solution to said RBCs prior to said flowing.

12. The method according to claim 11, wherein said additive solution is selected from the group consisting of OFAS3, SAGM, PAGG-SM, AS-1, AS-3, SOLX, MAPS, and PAGG-GM.

13. The method according to claim 12, wherein said OFAS3 has a pH ranging from about 5.5 to about 7.5.

14. The method according to claim 13, wherein said OFAS3 has a pH of about 6.5.

15. The method according to claim 1, wherein said OCDD device further comprises a leukoreduction filter, and said method further comprises leukoreducing said RBCs.

16. The method according to claim 1, wherein said OCDD device further comprises a leukoreduction filter, and said method further comprises leukoreducing said oxygen or oxygen and carbon dioxide reduced red blood cells.

17. The method according to claim 1, wherein said OCDD device further comprises a plasma separator, and said method further comprises separating plasma from said RBCs prior to said flowing.

18. The method according to claim 1, wherein said one or more gas sensor assemblies further comprise temperature, gas flow rate, total pressure, and humidity detectors.

19. The method according to claim 1, wherein said oxygen or oxygen and carbon dioxide reduced red blood cells has a hemoglobin oxygen saturation level of less than 3%.

20. The method according to claim 1, wherein said oxygen or oxygen and carbon dioxide reduced red blood cells has a carbon dioxide partial pressure of less than 50 Torr at 37° C.

\* \* \* \* \*